(12) United States Patent
   Al-Arab

(10) Patent No.: US 10,219,954 B2
(45) Date of Patent: Mar. 5, 2019

(54) MEDICAL COMPRESSION GARMENT AND DONNING METHOD

(71) Applicant: Gayla Al-Arab, Gig Harbor, WA (US)

(72) Inventor: Gayla Al-Arab, Gig Harbor, WA (US)

( * ) Notice: Subject to any disclaimer, the term of this patent is extended or adjusted under 35 U.S.C. 154(b) by 183 days.

(21) Appl. No.: 15/183,650

(22) Filed: Jun. 15, 2016

(65) Prior Publication Data
   US 2017/0360619 A1   Dec. 21, 2017

(51) Int. Cl.
   *A61F 13/00*   (2006.01)
   *A61F 13/08*   (2006.01)
   *A41F 1/00*   (2006.01)
   *A41D 13/12*   (2006.01)
   *A41D 13/00*   (2006.01)

(52) U.S. Cl.
   CPC ........ *A61F 13/085* (2013.01); *A41D 13/1281* (2013.01); *A41F 1/00* (2013.01); *A41B 2300/326* (2013.01); *A41D 13/00* (2013.01); *A41D 13/1263* (2013.01); *A41D 2400/44* (2013.01)

(58) Field of Classification Search
   CPC .............. A61F 13/085; A41D 13/1281; A41D 13/1263; A41D 13/00; A41F 1/00; A41B 2300/326
   See application file for complete search history.

(56) References Cited

U.S. PATENT DOCUMENTS

| 628,335 | A | * | 7/1899 | Kreuder | A44B 18/0076 |
|---|---|---|---|---|---|
| | | | | | 24/697.2 |
| 4,644,589 | A | | 2/1987 | Pettis | |
| 4,914,756 | A | * | 4/1990 | Grassick | A41D 1/06 |
| | | | | | 2/227 |
| 4,937,887 | A | | 7/1990 | Schreiner | |
| 5,520,630 | A | | 5/1996 | Daneshvar | |
| 5,983,401 | A | * | 11/1999 | Ohara | A41D 1/06 |
| | | | | | 2/227 |
| 6,135,974 | A | | 10/2000 | Matz | |

(Continued)

FOREIGN PATENT DOCUMENTS

WO   2012168824 A1   12/2012

OTHER PUBLICATIONS

European Patent Office, Extended European Search Report, Sep. 19, 2017, pp. 1-8.

*Primary Examiner* — Khaled Annis
(74) *Attorney, Agent, or Firm* — Fulwider Patton LLP

(57) ABSTRACT

A medical compression garment is provided including a midline opening cut in a medial segment of the elastic garment, dividing its front fabric portion into first and second sections. Fasteners, such as hook-and-loop fasteners, are attached to the first and second sections which connect together to close the opening. Pulls may be included. To don the garment, a wearer places their legs into the garment and pulls the garment along the legs until its top is aligned with the groin. The wearer then inverts and pulls the first and second sections of the garment together and fastens them to close the opening. Afterwards, the wearer pulls up the garment until it reaches the waist. When the wearer subsequently wants to take off the garment, the wearer unfastens the first and second sections and pull the garment down from the waist. The garment thus facilitates the donning and removal process.

25 Claims, 12 Drawing Sheets

(56) References Cited

U.S. PATENT DOCUMENTS

| | | | |
|---|---|---|---|
| 6,253,424 B1 * | 7/2001 | Rainville-Lonn | A41C 3/02 |
| | | | 24/306 |
| 6,296,618 B1 | 10/2001 | Gaber | |
| 6,301,755 B1 | 10/2001 | Gaber | |
| 8,157,791 B2 | 4/2012 | Mancuso | |
| 8,181,280 B2 * | 5/2012 | Caliste | A41D 13/1254 |
| | | | 2/400 |
| 2005/0091804 A1 | 5/2005 | Joosten et al. | |
| 2007/0033696 A1 | 2/2007 | Sellier | |
| 2009/0254017 A1 | 10/2009 | Dumpson et al. | |
| 2010/0235964 A1 * | 9/2010 | Mickey | A41D 13/1254 |
| | | | 2/228 |
| 2011/0179555 A1 | 7/2011 | Bickley et al. | |
| 2012/0172922 A1 | 7/2012 | Sesi | |
| 2015/0237932 A1 * | 8/2015 | Carryl | A41D 13/129 |
| | | | 2/69 |
| 2015/0245676 A1 * | 9/2015 | Carryl | A41D 13/129 |
| | | | 2/69 |
| 2016/0008178 A1 | 1/2016 | Babic et al. | |

* cited by examiner

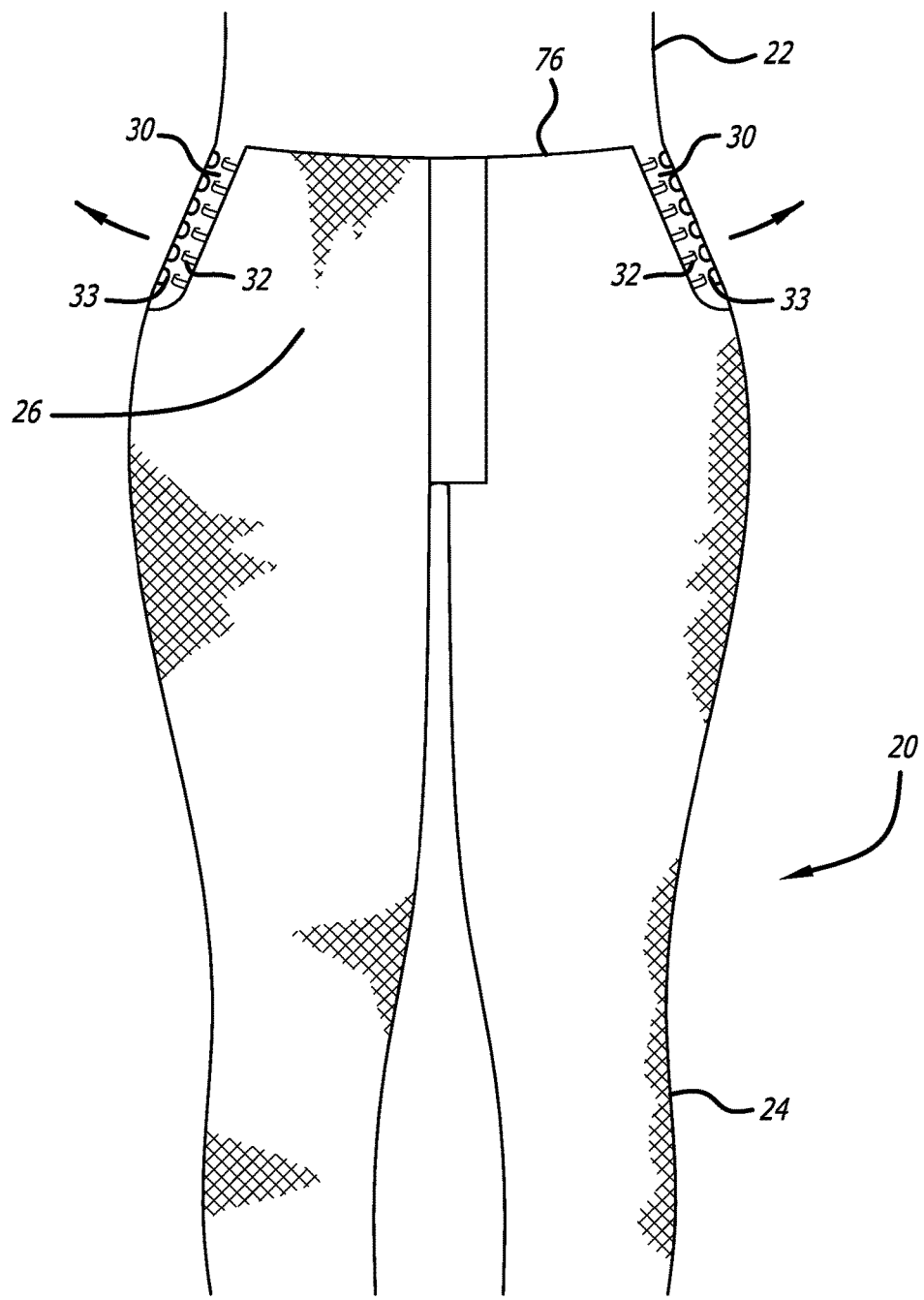

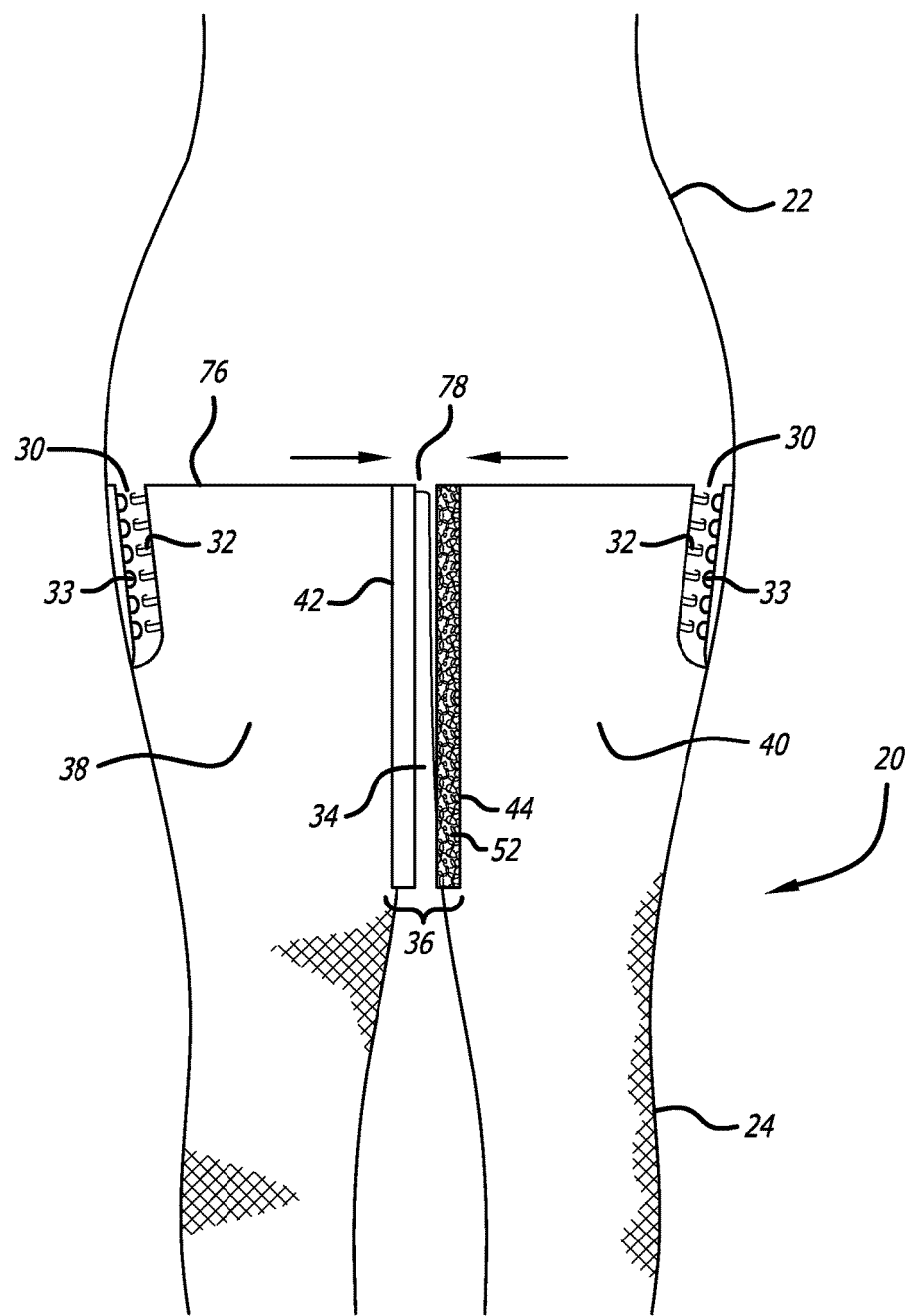

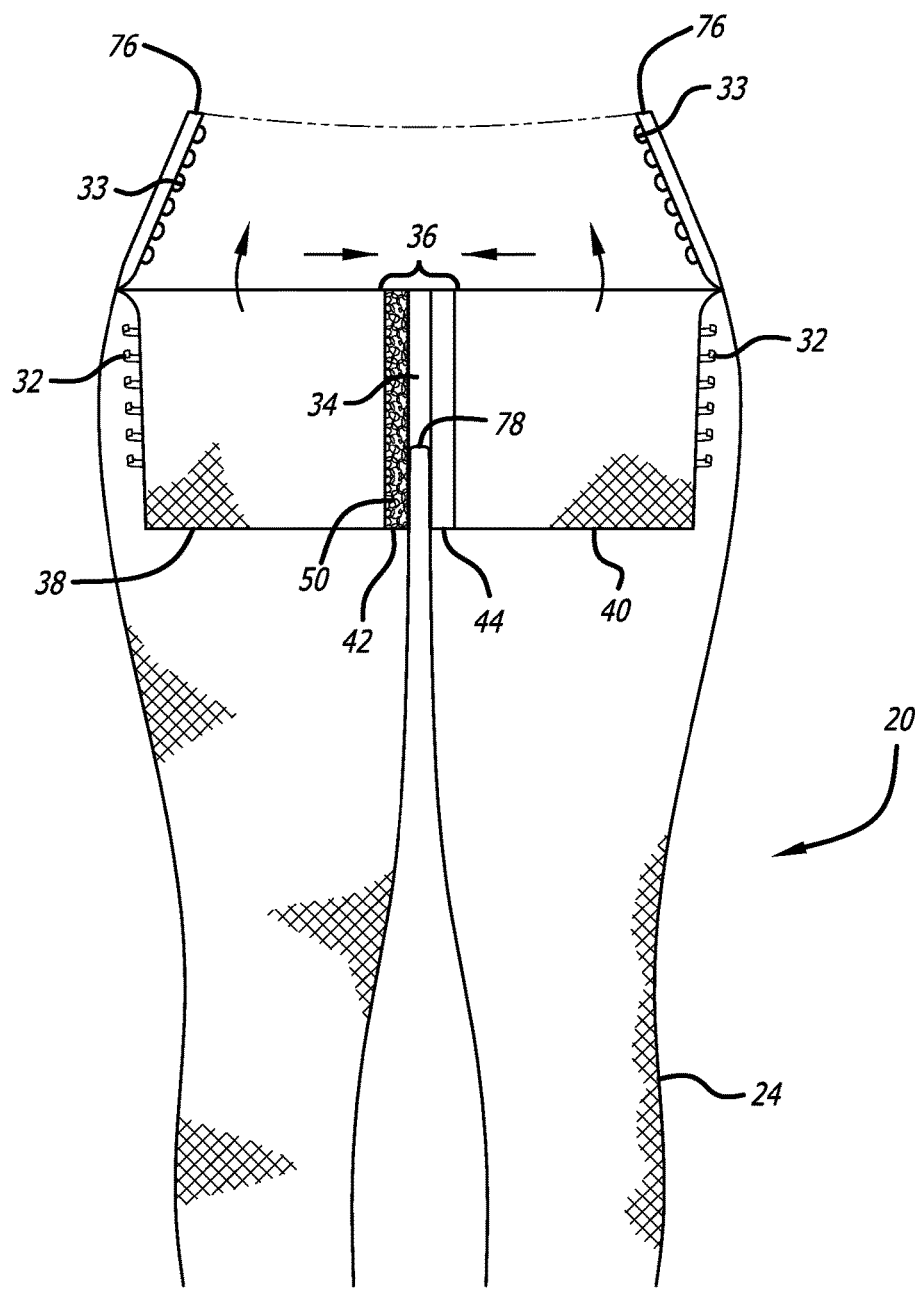

MEDICAL COMPRESSION GARMENT AND DONNING METHOD

BACKGROUND

The invention generally relates to compression garments, and more particularly relates to a medical compression garment that can easily be donned and removed.

Compression garments are generally provided to treat persons who have edema or swelling in a limb or other body part. Edema is a common condition that may occur as a result of surgeries such as water-assisted liposuction, certain medications or medical conditions, pregnancy, immobility, and severe injury such as from athletics or sports. Edema can also be caused by genetic underdevelopment, damage to lymphatic pathways, venous insufficiency, and disorders affecting body tissues such as lymphedema, lipedema, and varicose veins. Lymphedema in particular is a very serious condition that is caused by blockage or damage to the fluid drainage routes in the lymphatic system, resulting in fluid accumulation in body tissues and abnormal swelling in the limbs and other parts of the body. Lymphedema can also result from damage to the lymphatic pathways caused by other disorders, including lipedema, in which fat deposits and fluid accumulate in the lower body tissues. Lipedema is especially dangerous since it tends to be misdiagnosed as obesity, and therefore remains untreated for long periods of time. These disorders affect millions of people worldwide and detrimentally affect their physical and emotional quality of life.

Compression garments treat the effects of lymphedema, lipedema, and related disorders by limiting the amount of fluid building up in the limbs and flowing into the body tissues, and by encouraging the movement of fluid among the lymphatic pathways. These garments also provide support to loosened or sagging skin tissues caused by removal of a large amount of fluid from the limb, such as from surgery. To accomplish this, compression garments typically include a material or combination of materials that have compressive properties, such as those sold under the trademarks Lycra® or Spandex®. They are also designed to include graduated compression decreasing from the limb to the center of the body to direct fluid away from the limbs, and to have varying levels of pressure depending on the severity of the edema. For example, Class 1 compression garments (~15-20 mmHg) provide relief from minor edema, Class 2 compression garments (20-30 mmHg) provide relief from moderate varicose veins, lipedema and lymphedema, Class 3 compression garments (30-40 mmHg) provide relief from severe lymphedema, lipedema and deep venous thrombosis, and Class 4 compression garments (>40 mmHg) serve the most challenging cases. Consultation with a physician is typically required for Class 2 and higher compression garments.

As a result of their compressive properties, compression garments are typically very cumbersome to don and remove, unlike non-compressive clothing. Traditional compression garments must be pulled along the wearer's limbs transversely to the direction of the garments' pressure when putting on or taking off these garments. This can prove quite difficult where the wearer must be fitted in a high pressure garment (e.g. Class 3) due to severe edema, where the wearer has limited arm or hand strength, or where the wearer has limited mobility such as from arthritis. Medical professionals suggest various tips to wear these garments, such as putting it on immediately in the morning before a shower or bath, turning the garment inside-out and easing it up the limb one bit at a time, applying talcum powder to the limb, and avoiding moisturizers on the skin until the nighttime; however, attempting to remember all of these details can be daunting. While donning aids such as rubber gloves, stocking donners, lotions, and the like provide some assistance, such aids have to be purchased separately and can be relatively expensive. An easier way for a person to don and doff his or her own compression garment is therefore desired.

Also unlike non-compressive garments, compression garments require many important considerations to take into account in their manufacture and use. Compression garments must be perfectly fitted to the wearer; if they are too loose, they will not control swelling, and if they are too tight, they will restrict blood flow. Inaccurate measurements, or poorly manufactured compression garments, can cause severe pain and discomfort to the wearer. The class of compressive garment also determines its method of manufacture; circular knitted garments are produced in one piece with a fixed number of needles and without a seam, and therefore are only recommended for mild to moderate edema, while flat-bed knitted garments are produced in multiple pieces joined together with a seam, and are therefore recommended for moderate to severe edema. Wearers of compression garments must not fold over the top of the garment or turn back the hand-piece or foot of the garment when they are wearing it for long periods of time, since the amount of compression against the skin will double and possibly worsen the swelling. Wearers must also ensure they do not have wrinkles, creases, or folds in the material as they are wearing the compression garment, since these can damage the skin underneath the garment or cause a tourniquet effect that worsens the swelling.

In the case of wearers of lower body compression garments, the ability of these wearers to use the restroom is also an important issue. People who wear compression garments generally have to wear it several hours a day, for weeks, months, or years at a time, even for the rest of their lives. Due to the aforementioned difficulty in putting on and taking off these garments, compression garment manufacturers typically provide a fixed opening cut near the groin for the purpose of solid and liquid waste removal. Yet, requiring sole usage of the waste removal opening is undesirable since the compression garment may be soiled by solid or liquid waste that does not sufficiently clear the opening. Moreover, access to the opening for cleaning is limited when seated since the compression applied by the garment naturally forces the legs towards each other. To bypass these issues, medical professionals typically recommend people to wear thigh high or knee high compression stockings as they do not require removal prior to restroom usage. However, this alternative is inadequate for people who need to treat edema above the thighs, as is typically the case in severe lipedema, and it may have a tendency for slipping unless a silicone grip top band or adhesive is used. As a result, these people must wear lower body compression garments extending to the waist, such as compression pantyhose, leggings, tights, pants, trousers, shorts, and the like. An easier doffing solution facilitating restroom usage by wearers of these types of lower body compression garments is therefore desired.

Hence, there is a need for a medical compression garment that allows wearers to more easily don and remove the garment on their own. There is also a need for a medical compression garment that facilitates restroom usage without requiring sole usage of a fixed opening in the garment near the groin for solid and waste removal, thus reducing the risk of inadvertently soiling the garment. The present invention meets these and other needs.

SUMMARY OF THE INVENTION

The present invention is directed to a medical compression garment that facilitates the donning and removal process. A cut or opening is provided in a medial segment of a front fabric portion of the elastic garment extending from the waist down into the waste removal opening near the groin, thus dividing the front fabric portion into first and second sections. One or more fasteners are attached to the first and second sections which, when connected together, close the midline opening in the garment. The fasteners are preferably hook and loop fasteners, but can be any fastener known to those of ordinary skill in the art. Additionally, other components for facilitating closure of the midline opening may be provided, including additional fasteners and pulls that assist in pulling the first and second sections of the elastic garment together. The garment may also include side openings partially separating the front fabric portion from a rear fabric portion that can be narrowed or closed by fastening hook-and-eye closures that tighten the garment over the wearer's hips when worn.

When donning the garment, a wearer first places their legs into the garment and pulls up the garment along the legs until the top of the garment is aligned with the groin. The wearer then inverts the first and second sections of the front fabric portion, pulls the first and second sections of the front fabric portion together for example by using the pulls, and fastens them together using the hook and loop fasteners or other provided fastenings to close the midline opening in the garment. The wearer can more easily fasten the garment around the limbs as opposed to the waist, which is typically wider than the limbs. Afterwards, the wearer flips up the first and second sections of the front fabric portion, pulls up the garment until it reaches the waist, and fastens the hook-and-eye closures over the side openings of the garment. When the wearer subsequently wants to take off the garment, the wearer simply has to unfasten the first and second sections and pull the garment down from the waist.

In this way, the structure of the medical compression garment enables people with lipedema, lymphedema, varicose veins, and other edema to easily don and remove the garment. By initially putting on the garment unfastened, the wearer temporarily loosens the compression applied by the fabric and is allowed to more easily pull up the garment as opposed to traditional compression garments. When the garment is subsequently fastened, the compression provided by the fabric is fully realized, thus maintaining its medical effectiveness in treating edema in addition to facilitating the donning process. Moreover, since the wearer simply has to unfasten the garment from the waist all the way down to the fixed opening near the groin before using the restroom, the resulting ease in taking off the garment obviates the need for the wearer to rely solely on the waste removal opening for solid and liquid waste removal as typically required in conventional compression garments.

Additionally, by joining the midline opening with the waste removal opening, the present invention effectively transforms the circumference of the waste removal opening into linear form. As a result, when the garment is unfastened, the compression in the fabric is temporarily loosened enough to allow the wearer extra leg mobility or maneuverability. Moreover, when the wearer is seated in the restroom, the temporary reduction of compression in the unfastened garment prevents the legs from naturally closing together in contrast to conventional compression garments, thus providing increased cleaning access.

Accordingly, a medical compression garment is provided including an elastic compressive fabric that includes a front fabric portion and a rear fabric portion adapted to be worn around a body portion of a wearer. The front fabric portion includes a first section and a second section separated by an opening extending at least partially through a medial segment of the front fabric portion. The opening may be a midline opening, but is not required to be exactly at the midline of the garment. A first fastening is attached to an inner surface of the first section, and a second fastening is attached to an outer surface of the second section. The first section and second section of the front fabric portion are fastened together to close the opening by connecting the first fastening to the second fastening. For example, the first fastening and second fastening may be components of a hook and loop fastener, namely a hook portion attached to the inner surface of the first section, and a loop portion attached to the outer surface of the second section, respectively, that are connected together to close the opening.

Other fastening configurations may be provided. Particularly, a third fastening may be attached to an inner surface of the first section adjacent to the first fastening, and a fourth fastening may be attached to an outer surface of the second section adjacent to the second fastening. The first section and second section of the front fabric portion may then be fastened together to close the opening by connecting the first fastening to the second fastening and/or connecting the third fastening to the fourth fastening. For example, the third and fourth fastenings may be components of a second hook and loop fastener, namely a second hook portion attached to the inner surface of the first section adjacent to the first hook portion, and a second loop portion attached to the outer surface of a strip of fabric attached to the second section adjacent to the first loop portion, respectively, that are connected together to close the opening.

More particularly, a strip of fabric may be attached to the second section of the front fabric portion over at least a portion of the opening, and a second loop portion may be attached to an outer surface of the strip of fabric. In such case, the first section and second section of the front fabric portion may be fastened together by connecting the hook portion to either the loop portion or the second loop portion. Moreover, a second hook portion may be attached to the first section of the front fabric portion adjacent to the hook portion, and the first section and second section of the front fabric portion may be fastened together by connecting the second hook portion to either the loop portion or the second loop portion. Furthermore, the hook portion may be divided into hook portion segments spaced apart by gaps, and the first section and second section of the front fabric portion may be fastened together by connecting the hook portion segments to either the loop portion and the second loop portion.

Additionally, an additional or fifth fastening may be attached to an outer surface of one or more of the hook portion segments, and a complementary or sixth fastening may be attached to the outer surface of the second section of the front fabric portion. In such case, the first section and second section of the front fabric portion may be fastened together by connecting the hook portion segments to the loop portion and by connecting the fifth fastening to the sixth fastening.

To assist in pulling the first and second sections toward each other, at least one first pull may be attached to the first section of the front fabric portion, and at least one second pull may be attached to the second section of the front fabric portion. In such case, the first section and second section of the front fabric portion may be fastened together by pulling the first pull and the second pull toward each other to connect the hook portion to the loop portion.

The front fabric portion and the rear fabric portion may comprise a unitary elastic compressive fabric. Alternatively, the front fabric portion and the rear fabric portion may be partially separated by side openings extending in part through the elastic compressive fabric. In such case, fasteners such as hook-and-eye closures are used to fasten the front fabric portion and rear fabric portion together to narrow or close the side openings. For example, a plurality of fasteners such as hooks may be attached to one of the front fabric portion and the rear fabric portion, a plurality of complementary fasteners such as eyes may be attached to the other of the front fabric portion and the rear fabric portion, and the front fabric portion and rear fabric portion are fastened together to close the side openings by connecting the plurality of hooks to the plurality of eyes. Other types of fasteners known to those of ordinary skill in the art may also be used.

Also in accordance with the present invention, a method of donning a medical compression garment around a body portion of a wearer is provided. The method includes providing an elastic compressive fabric including a front fabric portion and a rear fabric portion, where the front fabric portion includes a first section and a second section separated by an opening extending at least partially through a medial segment of the front fabric portion; inserting limbs of the wearer into the elastic compressive fabric; pulling the elastic compressive fabric along the limbs until the top of the elastic compressive fabric aligns with the groin of the wearer; fastening the first section with the second section to close the opening in the front fabric portion; and pulling the elastic compressive fabric above the groin after the first section and second section are fastened together until the top of the elastic compressive fabric reaches the waist. The fastening is accomplished by connecting a first fastening attached to an inner surface of the first section with a second fastening attached to an outer surface of the second section.

Other variations of the method may exist. For example, the method may include inverting the first section and second section of the elastic compressive fabric prior to fastening the first and second sections together, and after fastening the first section with the second section, flipping up the first section and second section of the elastic compressive fabric before pulling the elastic compressive fabric above the groin towards the waist. Alternatively, the elastic compressive fabric may be pulled along the limbs until the top of the elastic compressive fabric reaches the waist before fastening the first and second sections together.

Additionally, the method may include narrowing a side opening extending partially through the elastic compressive fabric and separating the front fabric portion and rear fabric portion, after the elastic compressive garment reaches the waist, by connecting a plurality of hooks attached to either the front fabric portion or the rear fabric portion to a plurality of eyes attached to the other of the front fabric portion and the rear fabric portion.

Various fastening steps in the method are provided. For example, the fastening step of the method may include connecting a hook portion attached to the inner surface of the first section to a loop portion attached to the outer surface of the second section, where the first fastening and second fastening are components of a hook and loop fastener.

Moreover, the fastening step of the method may include connecting the hook portion to a second loop portion attached to an outer surface of a strip of fabric attached to the second section of the front fabric portion over at least a portion of the opening. Furthermore, the fastening step of the method may include connecting a second hook portion attached to the first section of the front fabric portion, adjacent to the hook portion, to either the loop portion or the second loop portion. Additionally, where the hook portion is divided into hook portion segments spaced apart by gaps, the fastening step may include connecting the hook portion segments to either the loop portion or the second loop portion, and may further include connecting an additional fastening attached to an outer surface of one or more hook portion segments with a complementary fastening attached to the outer surface of the second section of the front fabric portion. Finally, where a first pull is attached to the first section of the front fabric portion, and a second pull is attached to the second section of the front fabric portion, the fastening step of the method may include connecting the hook portion to the loop portion after pulling the first pull and the second pull toward each other.

Other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 10 is a front elevational view of the medical compression garment as it is being donned according to the method of FIG. 6, where the garment has successfully been pulled up to the waist, and where side openings in the garment are in the process of being narrowed from fastening of hook-and-eye closures connecting the front and rear fabric portions of the garment.

FIG. 11 is a front elevational view of the medical compression garment as it is being donned according to a variation of the method of FIG. 6, where the first and second section of the front fabric portion have already been flipped up from their inverted state at the groin and are in the process of being pulled toward each other for fastening.

FIG. 12 is a front elevational view of the medical compression garment as it is being donned according to an alternate variation of the method of FIG. 6, where the garment has been pulled along the legs past the groin all the way up to the waist, the first and second section of the front fabric portion have been inverted, and the first and second section are in the process of being pulled toward each other for fastening.

DETAILED DESCRIPTION OF THE PREFERRED EMBODIMENTS

Figure 1:
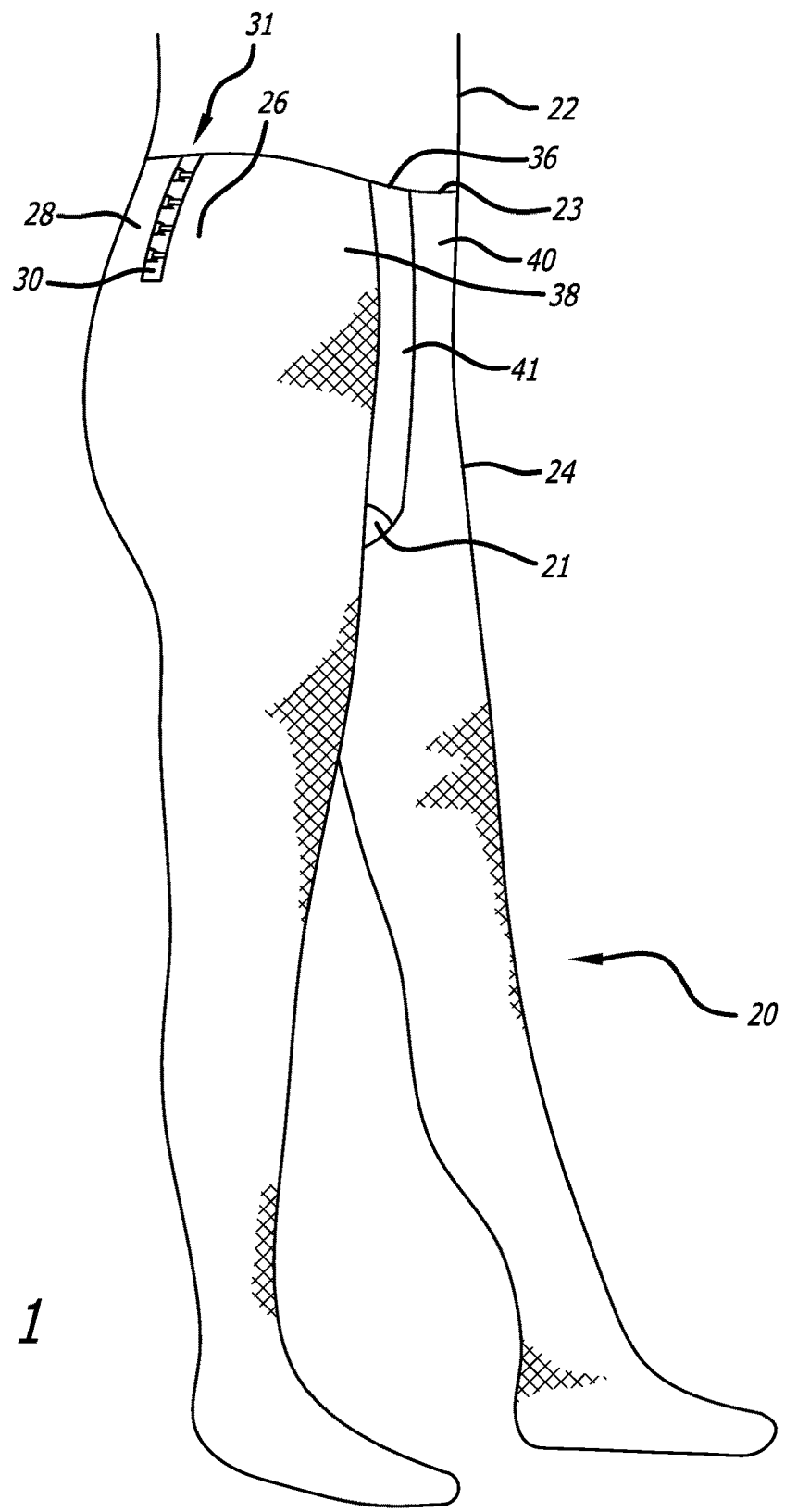
FIG. 1 is a perspective view of a medical compression garment as it is worn according to a preferred embodiment of the present invention.
Figure 2:
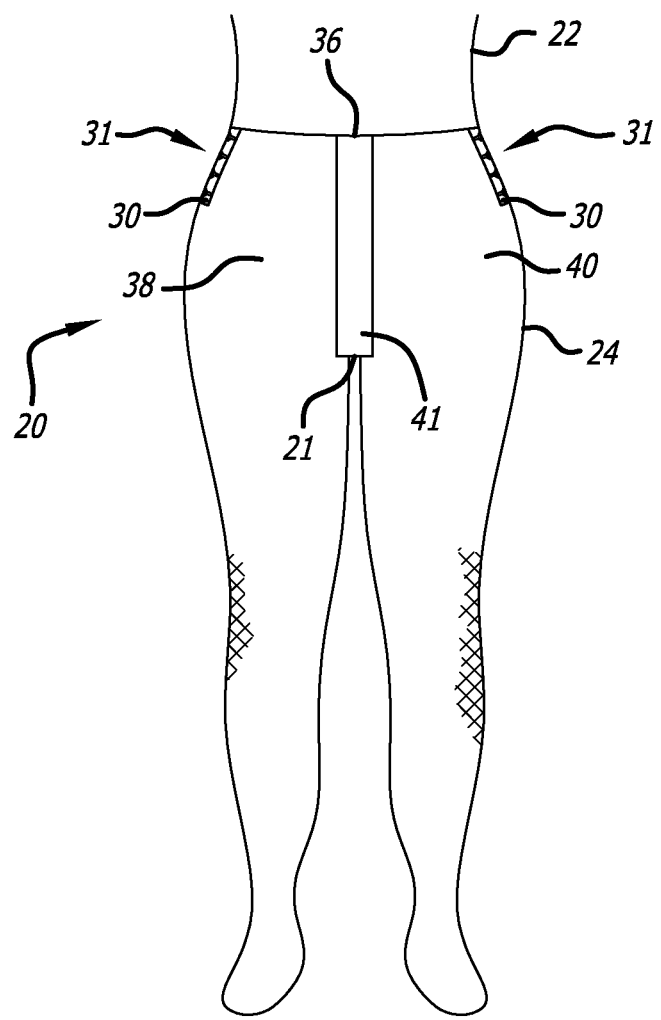
FIG. 2 is a front elevational view of the medical compression garment of FIG. 1.

Referring now to the drawings, FIGS. 1 and 2 illustrate a medical compression garment 20 according to a preferred embodiment of the present invention that is adapted to be worn around a body portion 22 of a wearer, depicted here as the wearer's lower body portion. The garment 20 may be compression pantyhose as depicted in the Figures, compression leggings, or any other garment extending to the wearer's waist 23. The garment 20 also generally includes a waste removal opening 21 for removal of solid and liquid waste.

The medical compression garment 20 includes an elastic compressive fabric 24 having a front fabric portion 26 and a rear fabric portion 28 made from materials conventionally used in compression garments. In the embodiment shown in the Figures, the front fabric portion 26 and rear fabric portion 28 are partially separated by side openings 30 extending from the waist in part through the fabric. These side openings 30 provide relief over the hips to assist the wearer in donning the garment 20, and are typically provided in post-surgical compression garments. Side fasteners 31, such as hook-and-eye closures, are complementarily attached to the front and rear portions of the fabric 24 near the side openings 30 for the wearer to fasten and tighten the garment around the hips when worn. For example, as denoted in FIG. 3, a plurality of hooks 32 may be attached to the front fabric portion 26 that interconnect with a plurality of eyes 33 attached to the rear fabric portion 28, or vice-versa. Alternatively, the garment may not include side openings 30 or complementary side fasteners 31, but instead comprise a unitary elastic compressive fabric formed by the front and rear fabric portions, as is generally the case in compression pantyhose.

A cut or opening 34 (denoted in FIG. 8) is made through a medial segment 36 of the front fabric portion 26, preferably through the midline of the garment and extending from the waist to the waste removal opening 21 near the groin, that separates and divides the front fabric portion 26 into a first section 38 and a second section 40. The intersection of the midline opening 34 with the waste removal opening 21 has the effect of transforming the waste removal opening 21 into linear form, thereby loosening the compression of the fabric 24 enough to allow the wearer extra leg mobility or maneuverability while seated in the restroom. Fasteners (not shown) are attached to the first section 38 and second section 40 for use in fastening the first and second sections together to close the opening 34 in the garment. While the elastic compressive fabric 24 may be stretched to fasten the first and second sections together, this may be difficult in situations where the wearer's edema is severe. As a result, material 41 is preferably attached to first section 38 so that the first section 38 extends over the opening 34 and thus can easily be fastened to second section 40. While the Figures illustrate first section 38 and second section 40 being on the right and left-hand sides of the wearer, respectively, their positions can be reversed.

Figure 3:
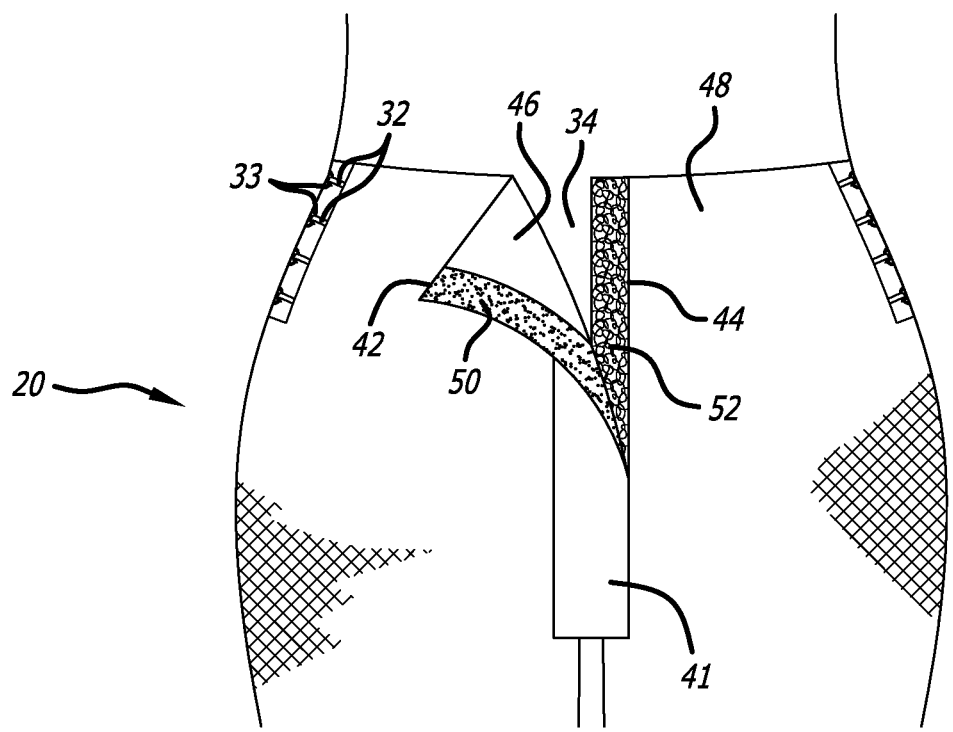
FIG. 3 is a front elevational, close up view of the medical compression garment of FIG. 1, illustrating a hook and loop fastener applied to a first and second section of a front fabric portion of the garment for closing an opening in a medial segment of the garment.
Figure 4:
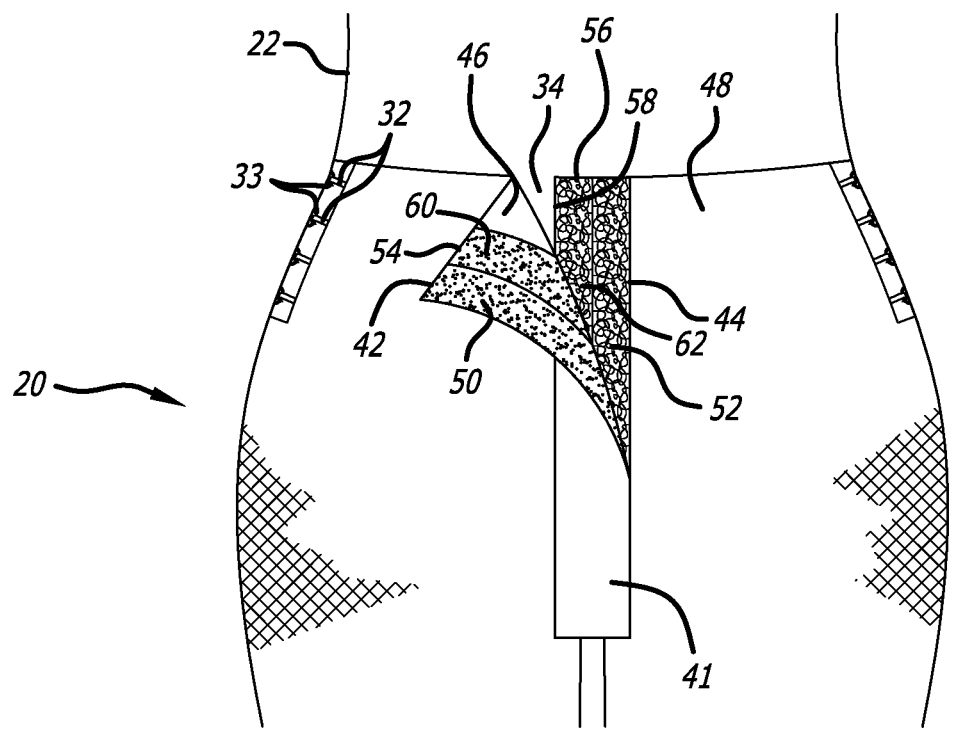
FIG. 4 is a front elevational view of the medical compression garment depicted in FIG. 3, further including a strip of fabric disposed over the opening in the medial segment of the garment, and a second hook and loop fastener to assist in closing the opening that is applied to the strip of fabric and to the first section of the front fabric portion of the garment.
Figure 5:
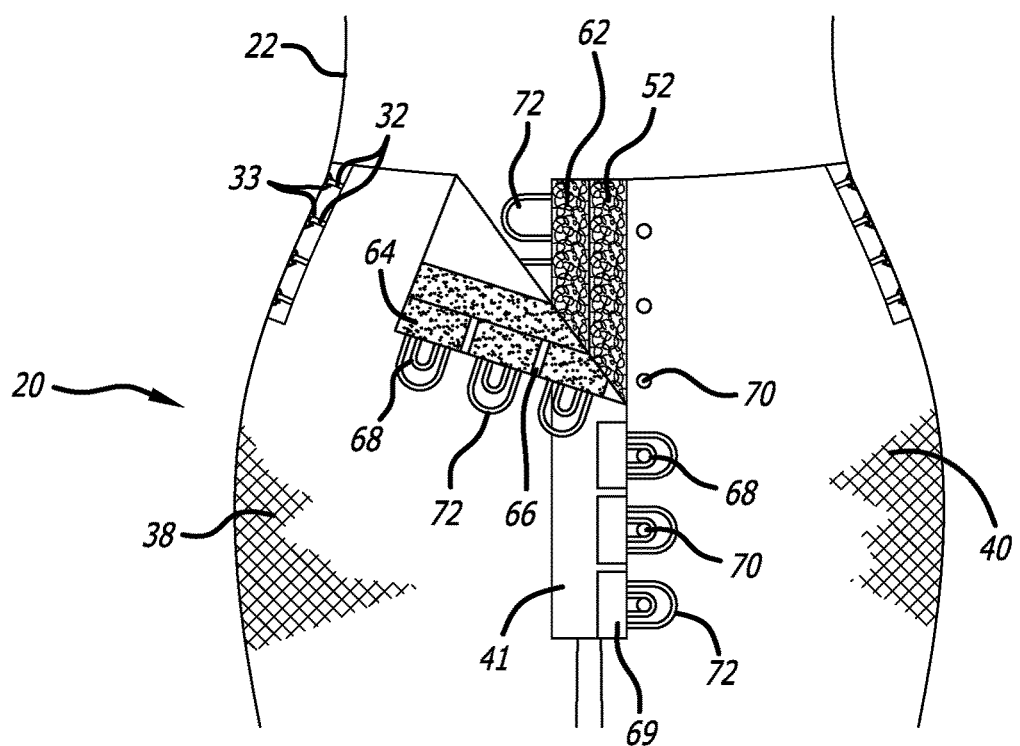
FIG. 5 is a front elevational view of the medical compression garment depicted in FIG. 4, where a hook portion of the hook and loop fastener is divided into hook portion segments and further including pulls, buttons, and loops attached to the first and second section of the front fabric portion of the garment to assist in closing the opening in the medial segment of the garment.

FIGS. 3-5 illustrate various fastening configurations of garment 20 used for closing the opening 34. In the embodiment of FIG. 3, a first fastening 42 is attached to the first section 38 of the front fabric portion 26, and a second fastening 44 is attached to the second section 40 of the front fabric portion 26. For example, fastening 42 can be attached to the inner surface 46 of the first section 38 extended by material 41, and fastening 44 can be attached to the outer surface 48 of the second section 40. Fastenings 42 and 44 are configured to connect with each other to fasten the first and second sections and close the opening 34. For example, fastenings 42 and 44 may respectively take the form of a hook portion 50 and a loop portion 52, or vice-versa, which function together as a hook and loop fastener, such as that marketed under the trademark Velcro®. In such case, a single hook portion and loop portion having lengths of approximately two inches are sufficient to close the opening 34, although other lengths may be contemplated. Alternatively, other known fastening mechanisms to those of ordinary skill in the art can be used.

Turning now to FIG. 4, an additional fastening configuration for garment 20 may be provided to assist the wearer in closing the opening 34. In this variation, a third fastening 54 is attached to the first section 38 of the front fabric portion 26, for example, on the inner surface 46 of the first section 38 adjacent to fastening 42. Complementary to fastening 54, a strip of fabric 56 is attached to the second section 40 of the front fabric portion 26 over at least a portion of the opening 34, and a fourth fastening 58 is attached to the strip of fabric 56. Fastenings 54 and 58 are configured to connect with each other to fasten the first and second sections together and close the opening 34 along with, or in lieu of, fastenings 42 and 44. For instance, fastenings 54 and 58 may respectively take the form of a second hook portion 60 and second loop portion 62, or vice-versa, which function together as a hook and loop fastener, such as that marketed under the trademark Velcro®, although other known fastening mechanisms can be used. The addition of fastenings 54 and 58 enable the medical compression garment 20 to be easily fastened over a body portion 22 with greater swelling than fastenings 42 and 44 by themselves would allow.

FIG. 5 illustrates a further fastening configuration for the medical compression garment 20. In this embodiment, hook portion 50 is divided into hook portion segments 64, spaced apart by gaps 66, that can individually be fastened to loop portions 52 or 62. This structure is particularly useful in facilitating closure of the opening 34 for those with severe edema, since it is easier for such wearers to fasten individual hook portion segments 64 as opposed to fastening the entire hook portion 50 all at once. Additionally, while three hook portion segments are preferred, any number of hook portion segments (such as the six shown in FIG. 5) can be used.

Moreover, to more easily facilitate closure of the opening 34, fifth fastenings 68 are attached to one or more of the hook portion segments 64, for example, on an outer surface 69 of the hook portion segments 64. These additional fastenings 68 mate with sixth fastenings 70 attached to the outer surface 48 of the second section 40 of the front fabric portion 26. For example, additional fastenings 68 and complementary fastenings 70 may be buttonholes (e.g. elastic loops) and buttons, respectively, as shown in FIG. 5, although other fasteners known to those of ordinary skill in the art can be used. Fastenings 68 and 70 may serve as backup fasteners maintaining closure of the opening 34 if, for example, hook portion segments 64 and loop portion 52 inadvertently come apart, or hook portion 60 and loop portion 62 inadvertently come apart. Additionally, pulls 72 may be optionally attached to both the first section 38 and second section 40 of the front fabric portion 26. These pulls 72 assist in closure of the opening 34 by allowing the wearer to more easily pull the first and second sections 38, 40 toward each other to enable the hook portions 50, 60 to be connected to the loop portions 52, 62. The pulls are preferably grosgrain but may be cloth or another type of non-stretch fabric.

Figure 6:
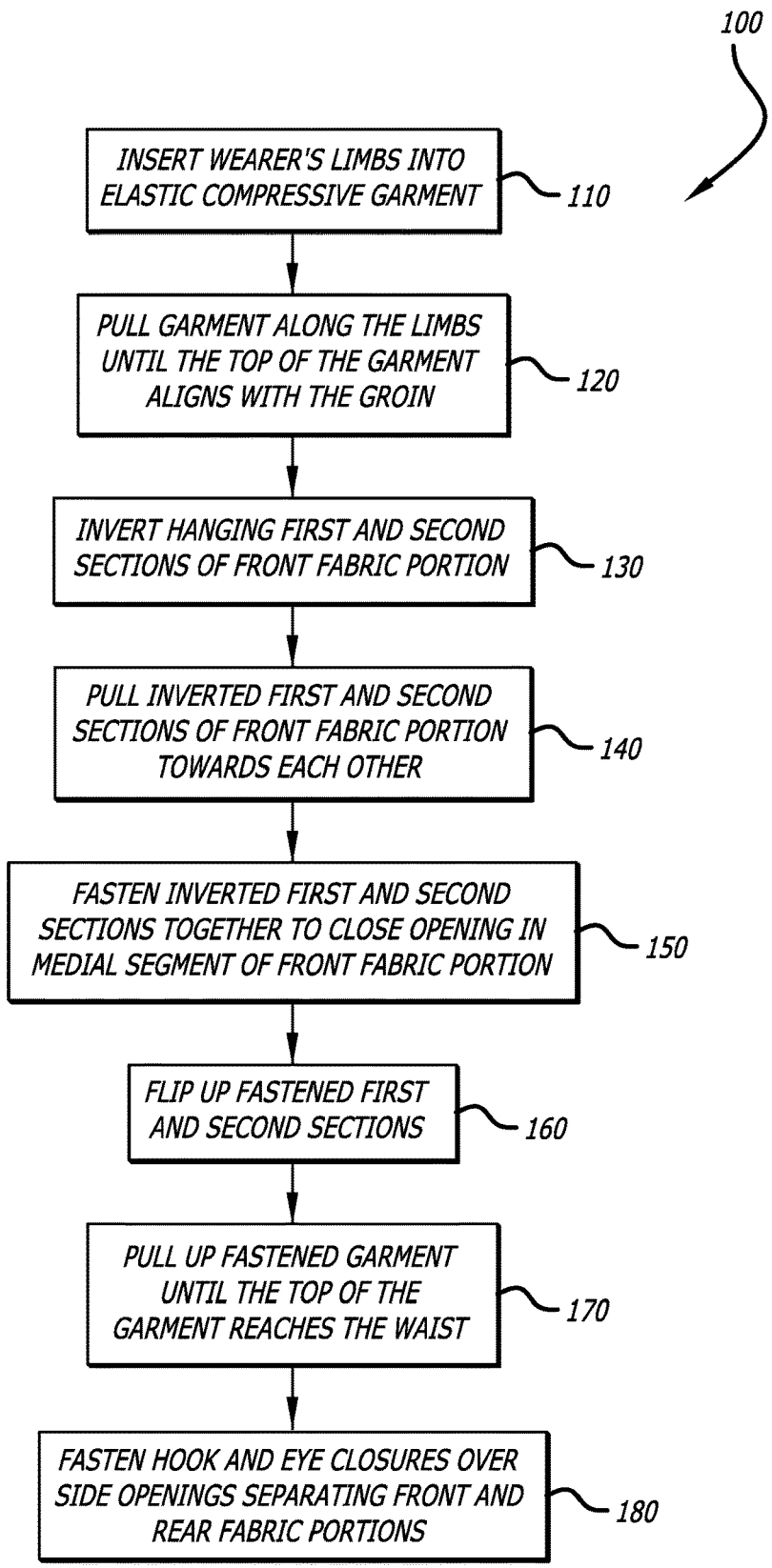
FIG. 6 is a schematic diagram illustrating a method of donning the medical compression garment of FIG. 1 according to a preferred embodiment of the present invention.

Turning now to FIG. 6, a method 100 is provided for donning the medical compression garment 20 according to a preferred embodiment of the present invention. Various steps of the donning process are illustrated for clarity in FIGS. 7-10. Exemplary variations of these steps are illustrated for clarity in FIGS. 11 and 12.

Figure 7:
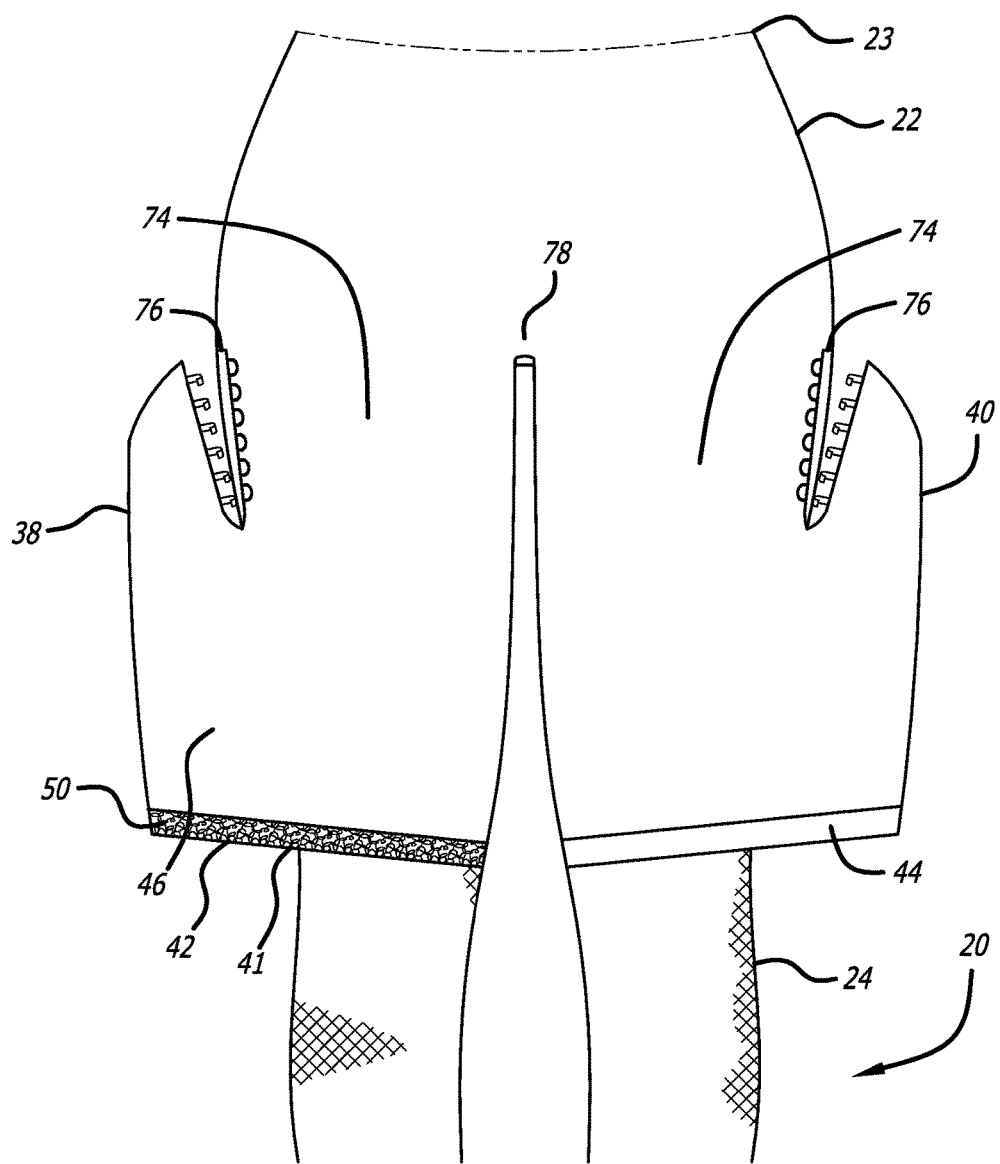
FIG. 7 is a front elevational view of the medical compression garment as it is being donned according to the method of FIG. 6, where the garment has been pulled along the legs to be aligned with the groin and the first and second sections of the front fabric portion are separated, unfastened, and hanging.

First, the wearer places their limbs 74 into the elastic compressive fabric 24 (110) and pulls the fabric along the limbs until a top 76 of the elastic compressive fabric 24 aligns with the wearer's groin 78 (120). The position of the garment after these steps are illustrated in FIG. 7, with the first section 38 and second section 40 of the front fabric portion 26 separated, unfastened, and hanging. While FIG. 7 illustrates that the top 76 of the fabric has been pulled up to the approximate point where the wearer's legs have come together, "alignment with the groin" as used herein is not limited to that point, but can include anywhere within the groin region bounded by the abdomen and the thighs.

Figure 8:
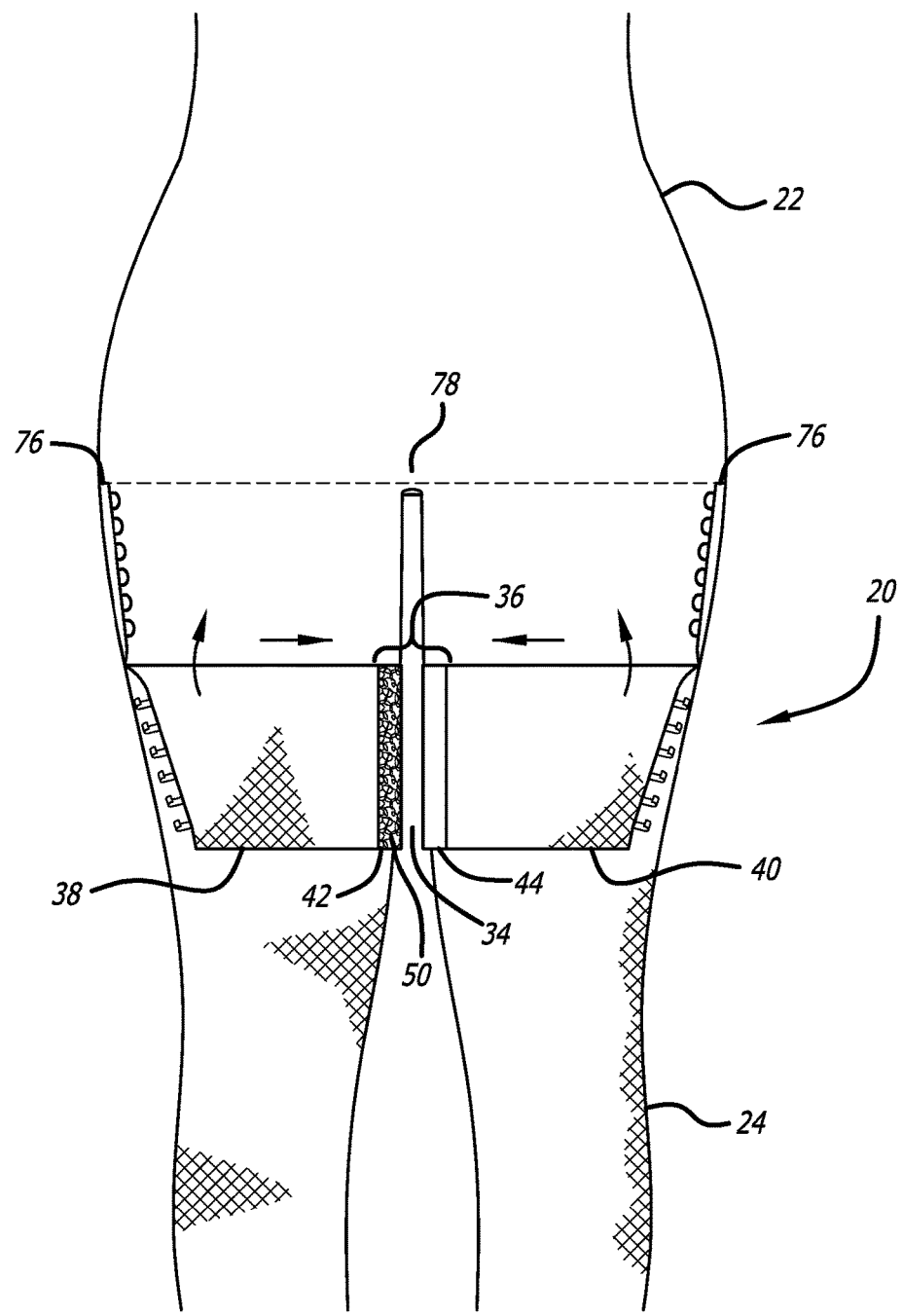
FIG. 8 is a front elevational view of the medical compression garment as it is being donned according to the method of FIG. 6, where the first and second section of the front fabric portion have been inverted and are in the process of being pulled toward each other.

Next, the wearer inverts the first section 38 and second section 40 (130) such that the garment appears as illustrated in FIG. 8. At this stage, the opening 34 in the medial segment 36 separating the first and second sections is apparent. If the elastic compressive fabric 24 includes side openings 30 with hook-and-eye closures or other side fasteners 31, these also preferably remain unfastened to relieve compression applied by garment 20 on the wearer's hips and ease the donning process.

Figure 9:
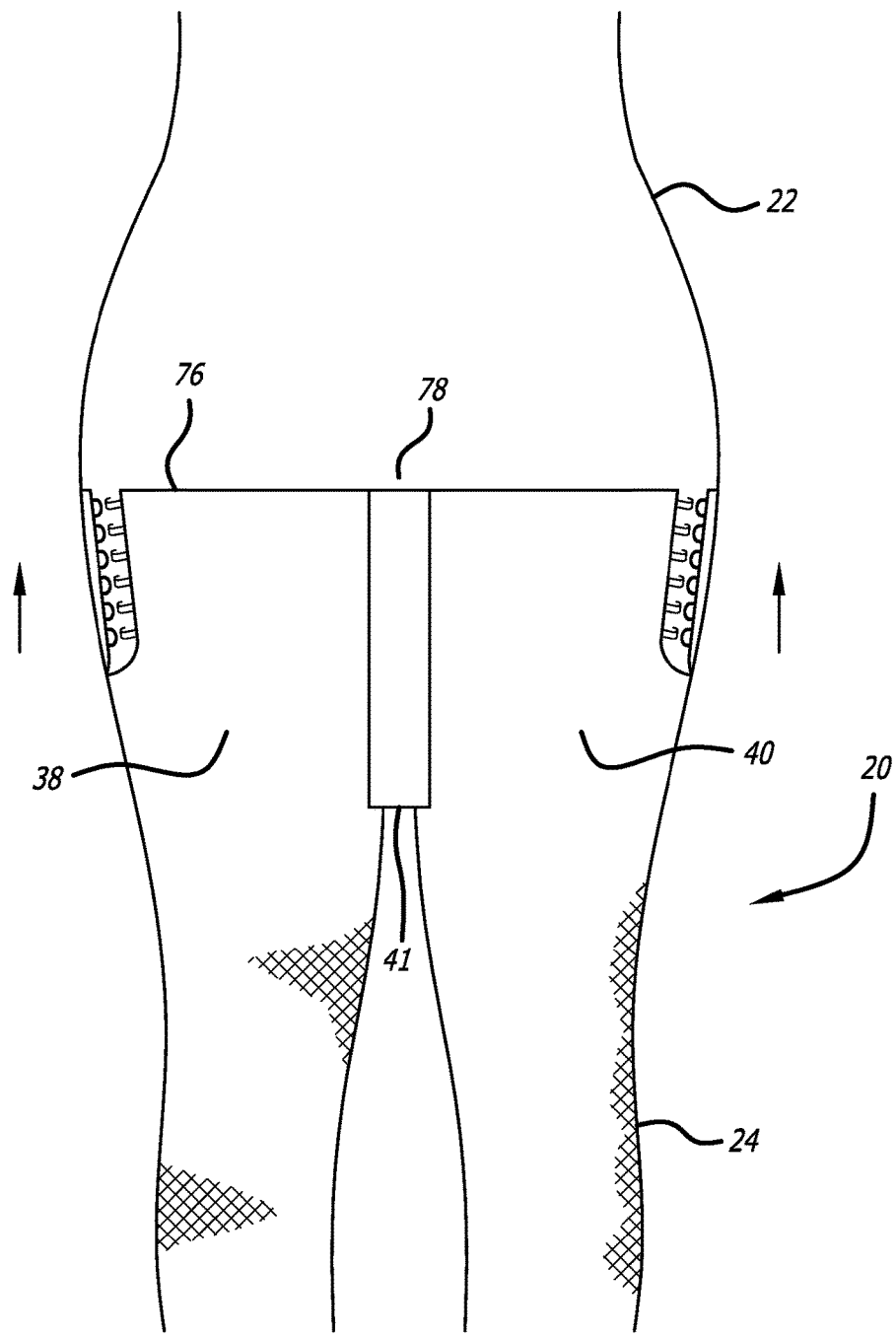
FIG. 9 is a front elevational view of the medical compression garment as it is being donned according to the method of FIG. 6, where the first and second section of the front fabric portion have successfully been fastened together and flipped up, and where the garment is in the process of being pulled up to the waist.

Once the first and second sections of the front fabric portion have been inverted, the wearer pulls the first section 38 and the second section 40 towards each other (140), fastens them together to close the opening 34 in the medial segment 36 of the front fabric portion 26 (150), and flips up the fastened first and second sections (160). FIG. 9 illustrates a result of these steps. The benefit of having previously aligned the top 76 of the garment 20 with the groin is evident at this stage, since the pulling and fastening steps are easier to perform around the wearer's limbs than around the wearer's hips or waist which tend to be more swollen from the wearer's edema.

The first and second sections may be fastened together using any of the fastening structures and configurations described above with respect to FIGS. 3, 4, and 5. For instance, the wearer may connect fastening 42 (e.g. hook portion 50 or hook portion segments 64) and/or fastening 54 (e.g. second hook portion 60) to either fastening 44 (e.g. loop portion 52) or fastening 58 (e.g. second loop portion 62). Additionally, the wearer may connect one or more fastenings 70 (e.g. buttons) to fastenings 68 (e.g. buttonholes). Pulls 72 can also be present as illustrated in FIG. 5 to assist in pulling the first and second sections towards each other in accordance with step (140).

After the first and second sections have been fastened together, the wearer pulls up the fastened garment 20 above the groin until the top 76 of the garment reaches the wearer's waist (170), as illustrated in FIG. 10. If the medical compression garment 20 includes side openings 30 with corresponding side fasteners 31, as is the case typically with post-surgical compression garments, the wearer subsequently fastens them together as previously described. For example, where fasteners 31 are hook-and-eye closures, the wearer fastens a plurality of hooks 32 attached to one of the first and second sections to a plurality of eyes 33 attached to the other of the first and second sections, thereby narrowing the separation between the front fabric portion 26 and rear fabric portion 28 and increasing the compression applied to the thighs (180). At this point, the garment 20 is fully worn.

While one embodiment of the donning method 100 has been described above, there are multiple ways a wearer can don the garment 20. For example, after pulling up the elastic compressive fabric 24 along the legs until the top 76 of the fabric aligns with the groin 78 as depicted in FIG. 7, the wearer may first flip up the first and second sections 38, 40 such as that illustrated in FIG. 11 before pulling the first section 38 and the second section 40 towards each other and fastening them together to arrive at the depiction referenced in FIG. 9. In an alternative example, the wearer may have sufficiently light edema to enable them to pull up the elastic compressive fabric 24 along the legs all the way to the waist, as illustrated in FIG. 12, before pulling together to fasten and flipping up (in whichever order) the first and second sections 38, 40. No further pulling of the garment along the limbs would be required in this case since the top 76 of the fabric will have already reached the wearer's waist. Any side openings 30 would then be subsequently fastened using side fasteners 31. These donning variations may be used by wearers with less severe edema in the legs and hips, for instance.

In some situations, the wearer may also desire to raise the compression garment 20 over the abdomen, for example, to treat edema resulting from a procedure of abdominal liposuction. In such case, the presence of a side opening 30 over each hip would be required for the garment, since if these side openings were non-existent or closed, the compression applied by the fabric 24 could render it difficult, if not impossible, for the wearer to pull the first and second sections 38, 40 together to close the opening 34 over the abdomen. This is another reason why the side fasteners 31 should be fastened only after the first and second sections 38, 40 have been pulled together, in accordance with the donning method 100.

When the wearer later wants to remove the garment, such as when using the restroom, the wearer simply needs to unfasten the first and second sections, such as by detaching the hook portions 50, 60 (or segments 64) from the loop portions 52, 62. Side openings 30 in the garment, if existing, may be widened by unfastening hook-and-eye closures 31 as well. Once the garment is completely unfastened, the compression applied by the garment will loosen considerably, thus enabling the wearer to easily pull the garment down along the limbs below the groin.

Consequently, by incorporating an opening 34 in the medial segment 36 of the medical compression garment 20 with the above-identified exemplary fastening configurations, the preferred embodiment of the present invention greatly facilitates donning and removal of the garment. As described above, traditional compression garments require the wearer to pull up the garment from the limbs all the way to the waist with fully applied compression forces, a feat that can be difficult to manage for persons with severe edema or limited strength or mobility. In contrast, the temporarily loosened compression provided by the preferred embodiment's initially unfastened configuration allows the wearer to more easily pull up the garment 20 before the wearer fastens and tightens the garment, thereby easing the garment donning process while ultimately maintaining the medical benefits provided by the garment's compressive forces. In addition, the wearer can simply take off the garment to use the restroom by unfastening the front fabric portion 26 and pulling down the garment below the groin. As a result, sole usage of a fixed opening near the groin for solid and liquid waste removal, as generally used in conventional lower body compression garments, is no longer required. Additionally, cleaning access to a wearer while seated in the restroom is not as limited as conventional compression garments due to the temporarily loosened compression from the garment's unfastened configuration.

While certain embodiments have been illustrated and described herein, those embodiments are not necessarily to be construed as advantageous over other embodiments for implementing the present subject matter. Other variations and equivalents are possible and should be considered within the scope of the present subject matter.

What is claimed is:

1. A medical compression garment adapted to be worn around a lower body portion of a wearer and to extend to the wearer's waist, the garment comprising:
    an elastic compressive fabric adapted to be worn around the lower body portion of a wearer, the elastic compressive fabric including a front fabric portion and a rear fabric portion, the front fabric portion including a first section and a second section separated by an opening extending at least partially through a medial segment of the front fabric portion;
    a waste removal opening distinct from the opening; and
    a first fastening attached to the first section and a second fastening attached to the second section, whereby the first section and second section of the front fabric portion are fastened together to close the opening by connection of the first fastening to the second fastening;
    wherein the first fastening and second fastening together comprise a hook and loop fastener including one of a hook portion or loop portion attached to the first section and the other of the hook portion or loop portion attached to the second section, whereby the first section and second section of the front fabric portion are fastened together by connection of the hook portion to the loop portion;
    wherein the hook portion is divided into hook portion segments spaced apart by gaps.

2. The medical compression garment of claim 1, wherein the front fabric portion and the rear fabric portion together form a unitary elastic compressive fabric.

3. The medical compression garment of claim 1, wherein the elastic compressive fabric includes the waste removal opening, and wherein the opening separating the first section and the second section of the front fabric portion extends through the medial segment of the front fabric portion and intersects the waste removal opening.

4. The medical compression garment of claim 1, further comprising a side opening extending partially through the elastic compressive fabric and separating the front fabric portion from the rear fabric portion, a plurality of side fasteners attached to one of the front fabric portion and the rear fabric portion, and a plurality of complementary side fasteners attached to the other of the front fabric portion and the rear fabric portion, whereby the front fabric portion and rear fabric portion are fastened together to narrow the side opening by connection of the plurality of side fasteners to the plurality of complementary side fasteners.

5. The medical compression garment of claim 1, further comprising a strip of fabric attached to the second section of the front fabric portion over at least a portion of the opening, and third fastening attached to the strip of fabric, whereby the first section and second section of the front fabric portion are fastened together by connection of the first fastening to at least one of the second fastening and the third fastening.

6. The medical compression garment of claim 5, further comprising a fourth fastening attached to the first section of the front fabric portion, whereby the first section and second section of the front fabric portion are fastened together by connection of the fourth fastening to at least one of the second fastening and the third fastening.

7. The medical compression garment of claim 1, further comprising an additional fastening attached to at least one of the hook portion segments and a complementary fastening attached to the second section of the front fabric portion, whereby the first section and second section of the front fabric portion are fastened together by connection of the hook portion segments to the loop portion and by connection of the additional fastening to the complementary fastening.

8. The medical compression garment of claim 1, further comprising a first pull attached to the first section of the front fabric portion and a second pull attached to the second section of the front fabric portion, whereby the first section and second section of the front fabric portion are fastened together by pulling of the first pull and the second pull toward each other to connect the first fastening to the second fastening.

9. A medical compression garment adapted to be worn around a lower body portion of a wearer and to extend to the wearer's waist, the garment comprising:
    an elastic compressive fabric adapted to be worn around the lower body portion of a wearer, the elastic compressive fabric including a front fabric portion and a rear fabric portion separated by a side opening extending partially through the elastic compressive fabric, and the front fabric portion including a first section and a second section separated by a midline opening extending at least partially through a medial segment of the front fabric portion;
    a waste removal opening distinct from the midline opening;
    a plurality of side fasteners attached to one of the front fabric portion and the rear fabric portion and a plurality of complementary side fasteners attached to the other of the front fabric portion and the rear fabric portion, whereby the front fabric portion and rear fabric portion are fastened together to narrow the side opening by connection of the plurality of side fasteners to the plurality of complementary side fasteners;

a strip of fabric attached to the second section of the front fabric portion extending over at least a portion of the midline opening; and a first fastening attached to the first section of the front fabric portion, a second fastening attached to the second section of the front fabric portion, a third fastening attached to the first section adjacent to the first fastening, and a fourth fastening attached to the strip of fabric, whereby the first section and second section of the front fabric portion are fastened together to close the midline opening by connection of at least one of the first and third fastening with at least one of the second and fourth fastening;

wherein the first fastening, second fastening, third fastening, and fourth fastening together comprise a plurality of hook and loop fasteners including a first hook portion attached to the first section of the front fabric portion, a first loop portion attached to the second section of the front fabric portion, a second hook portion attached to the first section of the front fabric portion adjacent to the first hook portion, and a second loop portion attached to the strip of fabric, whereby the first section and second section of the front fabric portion are fastened together by connection of at least one of the first and second hook portions to at least one of the first and second loop portions;

wherein the first hook portion is divided into hook portion segments spaced apart by gaps, and the first section and second section of the front fabric portion are fastened together by connection of the hook portion segments to at least one of the first and second loop portions.

10. The medical compression garment of claim 9, wherein the elastic compressive fabric includes the waste removal opening, and wherein the midline opening separating the first section and the second section of the front fabric portion extends through the medial segment of the front fabric portion and intersects the waste removal opening.

11. The medical compression garment of claim 9, wherein the plurality of side fasteners are a plurality of hooks and the plurality of complementary side fasteners are a plurality of eyes, whereby the front fabric portion and rear fabric portion are fastened together to narrow the side opening by connection of the plurality of hooks to the plurality of eyes.

12. The medical compression garment of claim 9, further comprising a fifth fastening attached to at least one of the hook portion segments and a sixth fastening attached to the second section of the front fabric portion, whereby the first section and second section of the front fabric portion are fastened together by connection of the hook portion segments to the first loop portion and by connection of the fifth fastening to the sixth fastening.

13. The medical compression garment of claim 9, further comprising a first pull attached to the first section of the front fabric portion and a second pull attached to the second section of the front fabric portion, whereby the first section and second section of the front fabric portion are fastened together by pulling of the first pull and the second pull toward each other to connect at least one of the first and second hook portions to at least one of the first and second loop portions.

14. A method of donning a medical compression garment around a lower body portion of a wearer, the garment being adapted to extend to the wearer's waist, the method comprising:

inserting limbs of the wearer into an elastic compressive fabric, the elastic compressive fabric including a front fabric portion and a rear fabric portion, the front fabric portion including a first section and a second section separated by an opening extending at least partially through a medial segment of the front fabric portion;

pulling the elastic compressive fabric along the limbs until a top of the elastic compressive fabric aligns with the groin of the wearer;

fastening the first section with the second section to close the opening in the front fabric portion by connecting a first fastening attached to the first section with a second fastening attached to the second section; and pulling the elastic compressive fabric above the groin after the first section and second section are fastened together until the top of the elastic compressive fabric reaches the waist of the wearer.

15. The method of claim 14, further comprising inverting the first section and second section of the elastic compressive fabric prior to performing the fastening step, and after fastening the first section with the second section, flipping up the first section and second section of the elastic compressive fabric before pulling the elastic compressive fabric above the groin towards the waist.

16. The method of claim 14, wherein the fastening step is performed after pulling the elastic compressive fabric along the limbs until the top of the elastic compressive fabric reaches the waist.

17. The method of claim 14, further comprising connecting a plurality of side fasteners attached to one of the front fabric portion and the rear fabric portion to a plurality of complementary side fasteners attached to the other of the front fabric portion and the rear fabric portion to narrow a side opening extending partially through the elastic compressive fabric and separating the front fabric portion and rear fabric portion after the elastic compressive fabric reaches the waist.

18. The method of claim 14, wherein the first fastening and second fastening together comprise a hook and loop fastener including a hook portion and a loop portion, and wherein the fastening step comprises connecting the hook portion attached to one of the first section or second section to the loop portion attached to the other of the first section or the second section.

19. The method of claim 18, wherein the hook portion is divided into hook portion segments spaced apart by gaps, and the fastening step comprises connecting the hook portion segments to the second section.

20. The method of claim 19, wherein the fastening step further comprises connecting an additional fastening attached to at least one of the hook portion segments with a complementary fastening attached to the second section of the front fabric portion.

21. The method of claim 14, wherein a strip of fabric is attached to the second section of the front fabric portion over at least a portion of the opening, and the fastening step comprises connecting the first fastening to a third fastening attached to the strip of fabric.

22. The method of claim 21, wherein a fourth fastening is attached to the first section of the front fabric portion, and the fastening step comprises connecting the fourth fastening to at least one of the second fastening and the third fastening.

23. The method of claim 14, wherein a first pull is attached to the first section of the front fabric portion, a second pull is attached to the second section of the front fabric portion, and the fastening step comprises connecting the first fastening to the second fastening after pulling the first pull and the second pull toward each other.

24. A medical compression garment adapted to be worn around a lower body portion of a wearer and to extend to the wearer's waist, the garment comprising:
 an elastic compressive fabric adapted to be worn around the lower body portion of a wearer, the elastic compressive fabric including a front fabric portion and a rear fabric portion, the front fabric portion including a first section and a second section separated by a midline opening extending at least partially through a medial segment of the front fabric portion;
 a waste removal opening distinct from the midline opening;
 a strip of fabric attached to the second section of the front fabric portion extending over at least a portion of the midline opening;
 a first fastening attached to the first section of the front fabric portion, a second fastening attached to the strip of fabric, a third fastening attached to the first section, and a fourth fastening attached to the second section adjacent to the strip of fabric, whereby the first section and second section of the front fabric portion are fastened together to close the midline opening by connection of at least one of the first and third fastening with at least one of the second and fourth fastening; and
 at least one first pull attached to the first section of the front fabric portion and at least one second pull attached to the second section of the front fabric portion, whereby the first section and second section of the front fabric portion are fastened together by pulling of the at least one first and second pulls toward each other to connect at least one of the first and third fastenings to at least one of the second and fourth fastenings;
 wherein the first fastening and second fastening together comprise a hook and loop fastener including one of a hook portion or loop portion attached to the first section and the other of the hook portion or loop portion attached to the strip of fabric, wherein the third fastening is one of a button or buttonhole attached to the first section and the fourth fastener is the other of the button or buttonhole attached to the second section adjacent to the strip of fabric, and whereby the first section and second section of the front fabric portion are fastened together by connection of the hook portion with the loop portion and the button with the buttonhole;
 wherein the hook portion is divided into hook portion segments spaced apart by gaps, and the first section and second section of the front fabric portion are fastened together by connection of the hook portion segments to the loop portion.

25. The medical compression garment of claim 24, further comprising a side opening extending partially through the elastic compressive fabric and separating the front fabric portion from the rear fabric portion, a plurality of side fasteners attached to one of the front fabric portion and the rear fabric portion, and a plurality of complementary side fasteners attached to the other of the front fabric portion and the rear fabric portion, whereby the front fabric portion and rear fabric portion are fastened together to narrow the side opening by connection of the plurality of side fasteners to the plurality of complementary side fasteners.

* * * * *